United States Patent [19]

Krüeger et al.

[11] 4,041,110

[45] Aug. 9, 1977

[54] MONOPHOSPHORIC ACID ESTERS OF HYDROXY ALKYL UREA COMPOUNDS

[75] Inventors: Friedrich Krüeger, Edingen; Güenter Schmidt, Ludwigshafen, both of Germany

[73] Assignee: Joh. A. Benckiser GmbH, Ludwigshafen (Rhine), Germany

[21] Appl. No.: 629,755

[22] Filed: Nov. 7, 1975

[30] Foreign Application Priority Data

Nov. 8, 1974 Germany .............................. 2453037

[51] Int. Cl.$^2$ .......................... C07F 9/141; C02B 5/06
[52] U.S. Cl. ..................................... 260/938; 252/175
[58] Field of Search ............... 251/175; 260/938, 978, 260/928, 929

[56] References Cited

U.S. PATENT DOCUMENTS 2,609,360  9/1952  Daul et al. ...................... 260/978 X
3,636,142  1/1972  DePierri ............................. 260/929
3,644,205  2/1972  DePierri ......................... 260/928 X

OTHER PUBLICATIONS

Cherbaliez, et al. "Index Chemic as", vol. 25, 81226, (1967).

*Primary Examiner*—Anton H. Sutto
*Attorney, Agent, or Firm*—Erich M. H. Radde

[57] ABSTRACT

Scale formation as well as deposition of incrustations in aqueous systems are prevented by the addition of a monophosphoric acid ester of a hydroxy alkyl urea compound or of salts of such an ester. Preferred esters of this type are the esters obtained by reacting hydroxyl alkyl urea compounds with urea phosphate. The esters are highly effective even when they are added in substoichiometric amounts calculated with respect to the scale and hardness causing compounds present in aqueous systems.

4 Claims, No Drawings

MONOPHOSPHORIC ACID ESTERS OF HYDROXY ALKYL UREA COMPOUNDS

BACKGROUND OF THE INVENTION

1. FIELD OF THE INVENTION

The present invention relates to a process of preventing scale formation and more particularly to an improved process of preventing scale formation in aqueous solutions by means of acidic phosphoric acid esters of hydroxy alkyl urea compounds, to compositions containing such acidic acid esters of phosphoric acid, to the acidic esters of phosphoric acid as such, and to a process of making same.

2. DESCRIPTION OF THE PRIOR ART

Acidic phosphoric acid esters of amino alcohols or amino polyalcohols have already been used for preventing scale formation in aqueous solutions. Such esters have proved of value as additives to natural salt-containing liquids, to circulating cooling fluids, to boiler fluids, and the like.

The esters, as they have been used heretofore for this purpose, were produced by phosphorylation of amino alcohols with polyphosphoric acids, phosphoric acid, or urea phosphate.

The scale formation preventing effect of the known phosphoric acid esters, however, is not fully satisfactory.

SUMMARY OF THE INVENTION

It is one object of the present invention to provide a simple and highly effective process of preventing scale formation by using monophosphoric acid esters of hydroxy alkyl urea compounds or salts of said esters in place of the known phosphoric acid ester.

Another object of the present invention is to provide a composition for preventing scale formation in aqueous solutions, said composition comprising as effective agent the monophosphoric acid esters of hydroxy alkyl urea compounds or the salts of such esters.

A further object of the present invention is to provide novel monophosphoric acid esters of hydroxy alkyl urea compounds and salts of such esters.

Still another object of the present invention is to provide a simple process of producing such novel monophosphoric acid esters of hydroxy alkyl urea compounds and salts of such esters.

Other objects of the present invention and advantageous features thereof will become apparent as the description proceeds.

The monophosphoric acid esters according to the present invention are obtained by phosphorylation of hydroxy alkyl urea compounds and preferably of hydroxy lower alkyl urea compounds. Urea phosphate has proved to be an especially advantageous phosphorylation agent because, when using this agent, there are obtained, in contrast to other phosphorylating agents, only monoesters and substantially no diesters. As a result thereof, the very important advantage is achieved that the reaction solutions resulting from such phosphorylation with urea phosphate can be used as such, i.e. without preceding purification and removal of the diester.

Of course, other phosphorylating agents such as phosphoric acid or polyphosphoric acids can also be used for producing the compounds according to the present invention, likewise phosphorus pentoxide.

The hydroxy alkyl urea compounds can readily be prepared by reacting urea with alkanolamines, whereby the reaction take place with splitting off of ammonia.

Suitable alkanolamines are mono- or di-alkanolamines with an alkyl chain containing 2 to 6 carbon atoms as well as alkoxylated alkanolamines. Suitable reactants are, for instance, mono-ethanolamine, di-ethanolamine, 2-hydroxy propylamine, bis-(2-hydroxy propyl) amine, 2,3-dihydroxy propylamine, 1,1,1-tris-(hydroxy methyl) amino methane, 3-hydroxy propylamine, 1-hydroxy-2-methyl isopropylamine, and the like.

The hydroxy alkyl urea reactants are compounds which are resistant against hydrolysis. They can be prepared in the pure state according to known methods and can then be reacted with urea phosphate. It is, however, also possible to condense the reaction products of alkanolamines and urea with urea phosphate without first isolating the alkanolamine-urea reaction products in the pure state. The reaction can, for instance, be carried out at about 100° C. to about 150° C. (temperature within the reaction mixture), while stirring. It is understood that the reaction mixture is to be heated at a lower temperature for a more prolonged period of time than at a higher temperature. Three hours to ten hours depending upon the reaction temperature are usually sufficient for completion of the reaction. After the reaction has been completed, the viscous reaction product is diluted with water to the desired concentration and can directly be employed as agent for preventing scale formation.

The monophosphoric acid ester according to the present invention exhibits an excellent stabilizing effect especially at a neutral pH-value of the aqueous solution. Therefore, they are especially suitable for stabilizing the degree of hardness of the water in circulating cooling fluids, in boiler fluids, in feed waters, and the like. The esters according to the present invention exhibit also an excellent anti-corrosive activity.

It is highly surprising that the monophosphoric acid esters of hydroxy alkyl ureas according to the present invention are superior to the known phosphoric acid esters of alkanolamines since urea itself does not have any scale formation preventing effect and since, therefore, it could not be expected that introduction of the urea group into the phosphoric esters would have any influence upon the scale formation inhibiting effect of such esters.

Substoichiometric amounts of said esters are sufficient to produce satisfactory results. Preferably the esters are added to the aqueous solutions in amounts of about 5 mg/l/ to about 500 mg/l. and preferably in amounts as low as 5 mg./l. to 50 mg./l.

The following Table I illustrates the excellent activity of the monophosphoric acid esters according to the present invention in comparison with the known phosphoric acid esters. The alkanolamines on the one hand and the corresponding urea derivatives on the other hand were reacted in parallel experiments with a phosphorylating agent. The resulting reaction products are compared in Table I with each other for their stabilizing effect.

According to this stabilization test, 2 mg. of the respective phosphoric acid esters are added to 100 ml. of water of a known hardness. The mixture is adjusted to a pH of 7.0 and is kept in a heating chamber at 80° C. for 16 hours. The resulting solution is filtered through two folded filters. The residual hardness is determined in the filtrate and is calculated as mval. alkaline earth metal ions per liter (1 mval of alkaline earth metal ions = 2.8° German hardness) according to the DIN 19,640 specification.

ample numbers given are those of the examples as described hereinafter.

| Phosphoric acid ester of: | Phosphorylating Agent: | mval. alkaline earth metal ions: |
|---|---|---|
| Ethanolamine $H_2N-CH_2-CH_2OH$ | urea phosphate | 3.50 |
| 2-Hydroxy ethyl urea $H_2N-\underset{\underset{O}{\parallel}}{C}-NH-CH_2CH_2OH$ (Example 1) | urea phosphate | 4.10 |
| Di-ethanolamine $HN(CH_2CH_2OH)_2$ | urea phosphate | 3.89 |
| N,N-Bis-(2-hydroxy ethyl) urea $H_2N-\underset{\underset{O}{\parallel}}{C}-N(CH_2CH_2OH)_2$ (Example 2) | urea phosphate | 4.36 |
| 2-(2-Hydroxy ethoxy)ethylamine $H_2NCH_2CH_2OCH_2CH_2OH$ | urea phosphate | 3.50 |
| 2-(2-Hydroxy ethoxy)ethyl urea $H_2NC-NHCH_2CH_2OCH_2CH_2OH$ $\underset{O}{\parallel}$ (Example 3) | urea phosphate | 4.21 |
| 2-Hydroxy propylamine $H_2NCH_2\underset{\underset{OH}{\mid}}{CH}CH_3$ | urea phosphate | 3.68 |
| N-(2-Hydroxy propyl) urea $H_2NC-NHCH_2\underset{\underset{OH}{\mid}}{CH}-CH_3$ $\underset{O}{\parallel}$ (Example 4) | urea phosphate | 4.21 |
| Bis-(2-hydroxy propyl)amine $HN(CH_2CH(OH)CH_3)_2$ | urea phosphate | 3.93 |
| N,N-Bis-2(2-hydroxy propyl) urea $H_2N-\underset{\underset{O}{\parallel}}{C}-N(CH_2CH(OH)CH_3)_2$ (Example 5) | urea phosphate | 4.10 |
| 3-Hydroxy propylamine $H_2N-CH_2-CH_2-CH_2-OH$ | urea phosphate | 3.75 |
| 3-Hydroxy propyl urea $H_2N-\underset{\underset{O}{\parallel}}{C}-NH-CH_2CH_2CH_2OH$ (Example 8) | urea phosphate | 4.61 |
| 1-Hydroxy-2-methyl isopropylamine $H_2N-\underset{\underset{CH_3}{\mid}}{\overset{\overset{CH_3}{\mid}}{C}}-CH_2OH$ | urea phosphate | 3.86 |
| 1-Hydroxy-2-methyl isopropyl urea $H_2N-\underset{\underset{O}{\parallel}}{C}-NH-\underset{\underset{CH_3}{\mid}}{\overset{\overset{CH_3}{\mid}}{C}}-CH_2OH$ (Example 9) | urea phosphate | 4.71 |
| 2-(2-Hydroxy ethoxy) ethylamine $H_2NCH_2CH_2OCH_2CH_2OH$ | Polyphosphoric acid | 3.28 |
| 2-(2-Hydroxy ethoxy)ethyl urea $H_2N-\underset{\underset{O}{\parallel}}{C}-NHCH_2CH_2OCH_2CH_2OH$ (Example 10) | Polyphosphoric acid | 4.14 |
| Bis-(2-hydroxy propyl)amine $HN(CH_2CH(OH)CH_3)_2$ | Orthophosphoric acid | 3.36 |
| Bis-(2-hydroxy propyl)urea $H_2NC-N(CH_2CH(OH)CH_3)_2$ $\underset{O}{\parallel}$ (Example 11) | Orthophosphoric acid | 3.71 |

TABLE I

Hardness stabilizing effect of the monophosphoric acid esters of hydroxy alkyl ureas according to the present invention compared with the known phosphoric acid ester of corresponding alkanolamines. The example numbers given are those of the examples as described hereinafter.

Table I clearly shows that the hardness stabilizing effect of the esters according to the present invention is very considerably superior to that of the known esters with alkanolamines or alkoxylated alkanolamines.

DESCRIPTION OF THE PREFERRED EMBODIMENTS

The following examples serve to illustrate the preparation of the monophosphoric acid esters according to the present invention and of solutions containing same for use as scale and deposit formation preventing agents without, however, limiting the same thereto.

EXAMPLE 1

104 g. (1.0 mole) of 2-hydroxy ethyl urea are mixed with 171.6 g. (1.1 moles) of urea phosphate while stirring. The reaction mixture is heated to 150° C. (temperature within the reaction mixture) for five hours. Ammonia and carbon dioxide escape with slight foam formation. After three to four hours the molten reaction mixture yields a viscous product which solidifies on cooling. The reaction product is dissolved in 100 ml. of water.

Yield: 276 g. of a 64% solution.

Said solution can directly be used without isolating the resulting monophosphoric acid ester.

EXAMPLE 2

74 g. (0.5 moles) of N,N-bis-(2-hydroxy ethyl) urea are mixed with 171.6 g. (1.1 moles) of urea phosphate. The reaction mixture is heated at 150° C. (internal temperature) for five hours, while stirring. A highly viscous melt is obtained after two to three hours. After cooling to a temperature between 100° C. and 90° C., the content of the reaction vessel is dissolved with 100 ml. of water.

Yield: 262 g. of a 62% solution.

The solution can directly be used.

EXAMPLE 3

148.0 g. (1.0 mole) of 2-(2-hydroxy ethoxy) ethyl urea and 171.6 g. (1.1 moles) of urea phosphate are heated in a glass flask to 130° C. (internal temperature), while stirring. After about five hours, the reaction mixture is cooled and the reaction product is dissolved in 200 ml. of water.

Yield: 466 g. of a 57% solution.

EXAMPLE 4

118 g. (1.0 mole) of N-(2-hydroxy propyl) urea are mixed with 171.6 g. (1.1 moles) of urea phosphate. The mixture is heated to 130° C. (internal temperature) for three hours, while stirring. Thereafter, the reaction mixture is cooled to 90° C. and the reaction product is dissolved in 200 ml. of water.

Yield: 438 g. of a 54.3% solution.

The solution can directly be used.

EXAMPLE 5

88.0 g. (0.5 moles) of N,N-bis(2-hydroxy propyl) urea and 171.6 g. (1.1 moles) of urea phosphate are heated in a flask provided with an ascending glass tube to 130° C. (internal temperature), while stirring. The reaction is completed after three hours. The reaction product is dissolved at 90° C. with 200 ml. of water.

Yield: 407 g. of a 50.8% solution.

EXAMPLE 6

67.0 g. (0.5 moles) of N-(2,3-dihydroxy propyl) urea are heated with 171.6 g. (1.1 moles) of urea phosphate at 130° C. (internal temperature) for three hours, while stirring. After cooling to a temperature between 100° C. and 90° C., the reaction product is dissolved with 200 ml. of water.

Yield: 376 g. of a 46.8% solution.

EXAMPLE 7

74.0 g. (0.5 moles) of N,N-bis-(2-hydroxy ethyl) urea and 171.6 g. (1.1 moles) of urea phosphate are heated to 100° C. (internal temperature) for seven hours, while stirring. After cooling to 90° C., the content of the reaction flask is dissolved with 200 ml. of water.

Yield: 391.0 g. of a 48.8% solution.

EXAMPLE 8

59.0 g. (0.5 moles) of 3-hydroxy propyl urea and 85.8 g. (0.55 moles) of urea phosphate are heated in a flask to 130° C. (internal temperature) for three hours, while stirring. After cooling to a temperature between 100° C. and 90° C., the content of the flask is dissolved with 100 ml. of water.

Yield: 216 g. of a 54.1% solution.

EXAMPLE 9

66.0 g. (0.5 moles) of 1-hydroxy-2-methyl isopropyl urea are heated with 85.8 g. (0.55 moles) of urea phosphate in a three-neck flask with ascending tube at 130° C. for three hours, while stirring. After cooling to about 90° C., the reaction product is dissolved with 100 ml. of water.

Yield: 217 g. of a 51.9% solution.

EXAMPLE 10

48.8 g. of polyphosphoric acid (corresponding to 0.55 moles of phosphoric acid) are placed into a threeneck round-bottom flask. 52.5 g. (0.5 moles) of 2-(2-hydroxy ethoxy) ethyl urea are added thereto, while stirring and the mixture is heated to 130° C. (internal temperature) for three hours. Thereafter, the reaction product is dissolved with 200 ml. of water.

Yield: 281 g. of a 28.8% solution.

EXAMPLE 11

119.7 g. (1.1 moles) of phosphoric acid (specific gravity: 1.75) are placed into a flask. 88.0 g. (0.5 moles) of bis-(2-hydroxy propyl) urea are added thereto, while stirring. The mixture is heated to 130° C. (internal temperature) for three hours. After cooling, the reaction product is dissolved with 200 ml. of water.

Yield: 373 g. of a 46.6% solution.

EXAMPLE 12

A mixture of 52.5 g. (0.50 moles) of di-ethanolamine and 30.0 g. (0.50 moles) of urea is heated to 110° C. (internal temperature) for about 4 hours while stirring. Ammonia set free during said reaction is drawn off by suction. Thereafter, 171.6 g. (1.1 moles) of urea phosphate are added thereto while stirring. On such addition the reaction mixture foams up for a short period of time. Heating is continued for 5 more hours. The resulting mixture is cooled below 100° C. and is diluted with 100 cc. of water. 262 g. of a 62% solution of phosphorylated dihydroxy ethyl urea are obtained.

Other hydroxy alkyl urea compounds with 2 to 6 carbon atoms in their alkyl chain as well as other hydroxy alkoxy alkyl urea compounds than those mentioned hereinabove can, of course, also be prepared and their esters with phosphoric acid can be used for the purpose of the present invention.

Preferably the hydroxy lower alkoxy lower alkyl urea compounds are obtained by reaction of the corresponding alkanolamines with ethylene oxide and/or propylene oxide followed by reaction of the resulting hydroxy ethoxy or hydroxy propoxy lower alkylamines with urea.

The polyphosphoric acid used in Example 10 is a polyphosphoric acid as it is described and obtained by FRITZ UHLIG in "Angew. Chem." vol. 66, No. 15, pages 435–436 (1954) and more particularly on page 436, left-hand column, second paragraph. Other polyphosphoric acids can, of course, also be used.

The hydroxy lower alkyl or hydroxy lower alkoxy lower alkyl urea phosphoric acid esters according to the present invention correspond to the following formula:

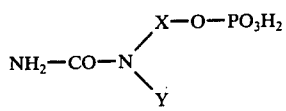

In said formula
X is lower alkyl or lower alkoxy lower alkyl with 2 to 6 carbon atoms preferably with 2 to 4 carbon atoms in the alkyl moieties of said substituent X, while
Y is hydrogen or the $-X-O-PO_3H_2$ group.

As shown in the Table and the examples, it is not necessary to isolate the monophosphoric acid esters according to the present invention. They can be used in the form of solutions obtained by dissolving the reaction products of hydroxy alkyl urea compounds or hydroxy alkoxy alkyl urea compounds with urea phosphate or other phosphorylating agents and using the resulting solutions as such as addition to aqueous systems in order to prevent scale formation and deposition.

Best scale formation inhibiting effects are achieved with aqueous systems of substantially neutral reaction. As is evident from the Table, addition of 20 mg. of the monophosphoric acid esters according to the present invention to one liter of aqueous systems to be treated is capable of retaining considerably larger amounts of hardness causing agents in solution than the heretofore used phosphoric acid esters of alkanolamines.

Preferably the compounds, i.e. the monophosphoric acid esters of the present invention and their waste soluble salts are added to the aqueous solutions to be stabilized, in the form of their concentration aqueous solutions, most advantageously in the form of solutions containing between about 25% and 65% of the compound. Suitable solutions are the reaction solutions obtained on reacting the alkanol urea compound or hydroxy alkoxy alkyl urea compound with the phosphorylating agent and dissolving the reactant product, after it has been cooled below 100° C., in the desired amount of water. It is not advisable to cool the reaction mixture to room temperature because the reaction product solidifies at such a low temperature and thus requires for complete dissolution too long a period of time. Cooling of the reaction mixture of about 80° C. to 90° C. has proved to be satisfactory.

As stated hereinabove, there can be used, in place of the monophosphoric acid esters according to the present invention, their water soluble salts such as the alkali metal or ammonium salts or the salts with organic amines. These salts are also most effective when used in aqueous systems of substantially neutral reaction.

As stated above, the monophosphoric acid esters according to the present invention are highly effective scale inhibitors when added to hard water containing scale forming ions. Their addition has proved of great value, for instance, in inhibiting scale formation in natural brines such as those formed in underground formations, for instance, in oil wells, in aqueous systems where hard water is employed, for instance, in boiler water, in circulating aqueous cooling fluids, and other aqueous systems of substantially neutral reaction.

Of course, many changes and variations in the reactants employed, the temperature, duration, and other reaction conditions in preparing the valuable monophosphoric acid esters of hydroxy alkyl urea compounds as well as many changes and variations in the conditions of using such esters for suppressing and preventing scale and deposit formation in aqueous systems, can be made by those skilled in the art in accordance with the principles set forth herein and in the claims annexed hereto.

We claim:
1. A phosphoric acid ester of a hydroxy alkyl urea compound of the formula

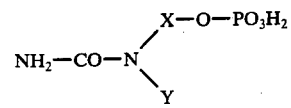

in which
X is a member selected from the group consisting of lower alkyl with 2 to 6 carbon atoms and lower alkoxy lower alkyl with 2 to 6 carbon atoms, while
Y is a member selected from the group consisting of hydrogen and the $-X-O-PO_3H_2$ group or the water soluble salts thereof.

2. The phosphoric acid ester of claim 1, said ester being the phosphoric acid ester of 2-(2-hydroxy ethoxy) ethyl urea.

3. The phosphoric acid ester of claim 1, said ester being the phosphoric acid ester of 1-hydroxy-2-methyl isopropyl urea.

4. The phosphoric acid ester of claim 1, said ester being the phosphoric acid ester of 3-hydroxy propyl urea.

* * * * *